(12) United States Patent
Choque et al.

(10) Patent No.: US 6,476,218 B1
(45) Date of Patent: Nov. 5, 2002

(54) METHOD OF PREPARING A MIXTURE OF MANNITOL AND SORBITOL BY CONTINUOUS HYDROGENATION OF GLUCOSONE

(75) Inventors: Jean-Christophe Choque, Lille (FR); Guy Fleche, Hazebrouck (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/552,468

(22) Filed: Apr. 18, 2000

(30) Foreign Application Priority Data

Apr. 27, 1999 (FR) .............................. 99 05308

(51) Int. Cl.⁷ .......................... C07H 1/00; C07H 15/20
(52) U.S. Cl. ...................... 536/124; 514/738
(58) Field of Search ................. 536/123.1, 123.13, 536/124; 514/738

(56) References Cited

U.S. PATENT DOCUMENTS 5,206,042 A * 4/1993 Dave et al. ................... 426/5

FOREIGN PATENT DOCUMENTS

WO 84 00778 3/1984

* cited by examiner

Primary Examiner—James O. Wilson
Assistant Examiner—Leigh C. Maier
(74) Attorney, Agent, or Firm—Henderson & Sturm LLP

(57) ABSTRACT

The invention relates to a method of preparing a mixture of mannitol and sorbitol, charactertized by the fact that continuous hydrogenation of glucosone with a solid matter content equal to at least 30%, preferably between 30 and 50%, is carried out in a succession of fixed catalyst beds disposed in series, which includes a first hydrogenation zone, made up of at least one fixed catalyst bed where hydrogenation is carried out at a temperature equal at the most to 80° C., preferably between 50 and 80° C., and a second hydrogenation zone, made up of at least one fixed catalyst bed where hydrogenation is carried out at a temperature equal to at least 80° C., preferably between 100 to 150° C.

18 Claims, No Drawings

METHOD OF PREPARING A MIXTURE OF MANNITOL AND SORBITOL BY CONTINUOUS HYDROGENATION OF GLUCOSONE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates to a method of preparing a mixture. of mannitol and sorbitol by hydrogenation of glucosone.

The present invention relates particularly to a method of preparing a mixture of mannitol and sorbitol containing a high proportion of mannitol, obtained by conducting the hydrogenation of glucosone in a continuous manner.

The present invention also relates to a continuous method of preparing said mixture of mannitol and sorbitol, by continuous hydrogenation of glucosone in a fixed catalyst bed, and more particularly the implementation of this continuous process in a succession of fixed catalyst beds disposed in series and in two reaction zones.

2. Description of the Prior Art

The industrial preparation of mannitol and sorbitol is conventionally carried out by catalytic hydrogenation of glucose, fructose or of a mixture of these two sugars.

Said mixture of glucose and fructose is conventionally obtained from invert sugar (glucose and fructose in a proportion of 50/50).

However, it is commonly acknowledged that the catalytic reduction of invert sugar, for example with Raney nickel, leads to the manufacture of a mixture of mannitol and sorbitol with a low proportion of mannitol, since one mole of mannitol is obtained for three moles of sorbitol.

Indeed, the catalytic hydrogenation of pure fructose already leads to an equimolar mixture of mannitol and sorbitol, whilst the catalytic hydrogenation of glucose directly yields sorbitol.

All the methods usually implemented by catalytic hydrogenation of fructose, or of the mixture of fructose and glucose, do not then make it possible to produce more than 50% mannitol.

In order to resolve this difficulty, the patent WO 84.00778 describes a method of preparing a mixture of mannitol and sorbitol, in which the mannitol represents at least 60% of the mixture, by the hydrogenation of glucosone with the aid of a Raney nickel catalyst.

Glucosone (also known under the names 2 keto-glucose or D-arabino-2-hexulosone) is conventionally obtained by oxidation of glucose by chemical means (by treating with oxygenated water or with copper acetate) or advantageously by enzymatic means (with the aid of a pyranose 2-oxidase) in order to lead to a product of high purity.

It is described in this patent that carrying out the glucosone hydrogenation in a discontinuous manner, whatever the solid matter content used may be, with a Raney nickel catalyst, makes it possible to prepare mixtures of mannitol and sorbitol containing variable proportions of mannitol, between 60 and 75%.

However, the hydrogenation conditions implemented in this patent application lead to the production first of all of a mixture of mannose, fructose and glucose from the glucosone, before continuing the hydrogenation makes it possible to obtain the mixture of mannitol and sorbitol. The reaction times for hydrogenating glucosone with a high solid matter content are very long and therefore disadvantageous.

Moreover, even if this discontinuous hydrogenation process makes it possible to obtain the mixture of mannitol and sorbitol, from a solution of glucosone with 30% solid matter, with a proportion of mannitol in said mixture of the order of 70%, this is only with a selectivity of the order of 97% and a mediocre productivity. Furthermore, the conversion rate is only 90%.

It is thus clearly apparent in prior art that the methods of discontinuous hydrogenation of glucosone with a high solid matter content do not make it possible to obtain a mixture of mannitol and sorbitol containing a high proportion of mannitol, with a high conversion rate, high selectivity and high productivity.

DETAILED DESCRIPTION OF THE INVENTION

The object of the invention is therefore to remedy this situation and to propose a means making it possible to achieve a better compromise between conversion rate, selectivity and productivity, and this for a high solid matter content of glucosone.

The present invention discloses that such a means could consist in a continuous process of catalytic hydrogenation of glucosone with a high solid matter content, conducted in specific conditions.

The subject matter of the present invention is precisely a method of preparing a mixture of mannitol and sorbitol, characterised by the fact that continuous hydrogenation of glucosone having a solid matter content equal to at least 10%, preferably between 30 and 50%, is carried out in a succession of fixed catalyst beds, disposed in series, which includes;

- a first hydrogenation zone, made up of at least one fixed catalyst bed, where the hydrogenation is carried out at a temperature equal at the most to 80° C., preferably between 50 and 80° C.,
- a second hydrogenation zone, made up of at least one fixed catalyst bed, where the hydrogenation is carried out at a temperature equal to at least 80° C., preferably between 100 and 150° C.

One chooses to prepare the solution to be hydrogenated with glucosone of very high purity, advantageously produced by enzymatic means from glucose by any means known to the expert.

By "high purity" is meant a glucosone content of the order of 100%.

The catalyst is selected from the group made up of palladium, nickel, ruthenium, platinum, rhodium, cobalt, copper, zinc, chromium, manganese, tungsten, and is preferably ruthenium.

In the method according to the invention, the catalyst is generally impregnated or co-exchanged on an inert medium, preferably chosen from the group made up of activated charcoal, peat, zeolites, aluminosilicates, titanium dioxide. By preference, it consists of activated charcoal.

The weight ratio catalyst/inert medium is advantageously established at a value of between 1 and 5%, preferably of the order of 2% as exemplified below.

It is also possible to use a catalyst including a promoting agent. This promoting agent can be chosen from the group made up of titanium, molybdenum and platinum.

The catalyst is disposed in a fixed bed in the form of a compact stack of particles, all placed on support grates in a hydrogenation reactor. Advantageously, a trickle-bed reactor is chosen.

In the sense of the invention, what is meant by "trickle-bed reactor" is a hydrogenation reactor in which a liquid phase containing the product to be hydrogenated and a gas phase circulate in a co-current or counter-current manner, preferably in a co-current manner from top to bottom, in a fixed bed of catalyst particles where the hydrogenation reaction takes place.

The flow rates of these two phases are adjusted to permit the liquid to trickle onto said catalyst particles and to ensure the best contact between the two phases, liquid and gaseous, on the one hand, and the solid phase of the catalyst on the other hand.

In an embodiment of the method according to the invention, one chooses to prepare a fixed bed made up of 200 l commercial catalyst, a rate of feeding the glucosone solution with a solid matter content of between 10 and 50% by weight, at a value of between 150 and 350 kg/h, and a quantity of hydrogen introduced into said trickle-bed reactor of the order of two to fifteen times the stoichiometry of the reaction.

In an embodiment of the method according to the invention, one chooses to use a continuous process of glucosone hydrogenation in a succession of fixed catalyst beds disposed in series and in at least two reaction zones.

The hydrogenation is thus advantageously carried out in a first reaction zone, made up of at least one fixed catalyst bed, so as to obtain a total conversion of the glucosone into a mixture of mannose, glucose and fructose, containing a high proportion of mannose, then in a second reaction zone, made up of at least one fixed catalyst bed, where the hydrogenation is carried out in such a way as to obtain a mixture of mannitol and sorbitol with a high conversion rate and high selectivity.

The present invention discloses that it is possible, contrary to what is established in prior art, to carry out the hydrogenation in a continuous manner and in two reaction zones, so as to separate the stage of producing the mixture of mannose, glucose and fructose from that of producing the mixture of mannitol and sorbitol, in order to obtain said mixture of mannitol and sorbitol with a high mannitol content never yet achieved, and with high productivity, high selectivity and a high conversion rate.

Catalysts of different nature can be used in each of the reaction zones. However, using a catalyst of the same nature in these two zones is preferred.

In the first reaction zone, the temperature conditions are adjusted so as to obtain high conversion, of the order of 100%, of the glucosone into a mixture of mannose, glucose and fructose, the proportion of mannose in the mixture being high.

In the sense of the invention, what is meant by "high proportion of mannose" is a mannose content equal to at least 70% by weight of the mixture.

Temperature conditions are also implemented which also limit, indeed eliminate, the conversion of the glucosone into fructose, and limit that of glucose.

The hydrogenation temperature in the first reaction zone is thus fixed at a value equal at the most to 80° C., preferably between 50 and 80° C.

In the second reaction zone, the temperature conditions are adjusted so as to obtain the mixture of mannitol and sorbitol, containing a high proportion of mannitol, with a conversion rate equal to at least 98%.

In the sense of the invention what is meant by a "high proportion of mannitol" is a weight ratio of mannitol over sorbitol equal to at least 3.5.

The hydrogenation temperature in the second reaction zone is thus fixed at a value equal to at least 80° C., preferably between 100 and 150° C.

In the method according to the invention, one chooses to carry out the hydrogenation in at least one fixed catalyst bed in which this pressure is greater than 50 bar.

By preference, the hydrogenation pressure is kept constant in the two reaction zones at a value of between at the most 50 bar and 150 bar, and is preferably between 55 and 100 bar.

The fixed catalyst beds are advantageously disposed in trickle-bed reactors. By choice, 200 l commercial catalyst particles are used, a rate of feeding the glucosone solution with a high solid matter content of between 10 and 50% by weight at a value between 150 and 350 kg/h, and a quantity of hydrogen between two and fifteen times the stoichiometry of the reaction.

Other characteristics and advantages of the invention will appear in reading the non-restrictive example described below.

EXAMPLE

The hydrogenation reaction is carried out in two trickle-bed reactors connected in series with an intermediate heat exchanger.

Each of the two reactors encloses a single fixed bed of a ruthenium catalyst on charcoal, in which hydrogen and the glucosone solution are made to circulate in a co-current manner from the top to the bottom of the said reactors.

Each fixed bed of ruthenium catalyst is made of a compact stack of cylindrical catalyst grains.

Each catalyst grain is composed of activated charcoal of the type NORIT RX08, in the form of a cylinder of 0.8 mm in diameter and between 1 and 5 mm in length, containing 2% by weight ruthenium.

Each reactor contains in the order of 200 l catalyst, disposed in a fixed bed of 30 cm in diameter and in the order of 3 m in height.

Simultaneously, the first hydrogenation zone is supplied with a glucosone solution with 30% solid matter, at a feed rate of 200 kg/h, and with hydrogen at the rate of 10 kg/h.

The operating pressure in the first reactor is 55 bar, and the temperature is fixed at 80° C.

The entry temperature of the second reactor is brought to 100° C. and the pressure kept at 55 bar.

At the exit of the first reactor, the conversion rate is 100% and the mixture of mannose, fructose and glucose presents the following composition: 74% by weight mannose, 8% by weight fructose and 16% by weight glucose.

At the exit of the second reactor, the conversion is 99%, and the mixture of mannitol over sorbitol presents a ratio of mannitol over sorbitol of 3.8.

What is claimed is:

1. A method of preparing a mixture of mannitol and sorbitol, wherein continuous hydrogenation of glucosone with a solid matter equal to at least 10% is carried out in a succession of fixed catalyst beds disposed in series, which includes:

a first hydrogenation zone, made up of at least one fixed catalyst bed, wherein hydrogenation is carried out at a temperature equal at the most to 80° C.; and a second hydrogenation zone, made up of at least one fixed catalyst bed, wherein the hydrogenation is carried out at a temperature equal to at least 80° C.

2. The method according to claim 1, wherein that the catalyst is selected from the group consisting of palladium, nickel, ruthenium, platinum, rhodium, cobalt, copper, zinc, chromium, manganese, tungsten, and is preferably ruthenium.

3. The method according to claim 1, wherein the hydrogenation is carried out in at least one fixed catalyst bed at a pressure greater than 50 bar.

4. The method according to claim 1, wherein the hydrogenation pressure in the two reaction zones is between 50 bar and 150 bar.

5. The method according to claim 1, wherein said solid matter is equal to between 30% and 50%.

6. The method according to claim 1, wherein in said first hydrogenation zone, said hydrogenation is carried out at a temperature between 50° C. and 80° C.

7. The method according to claim 1, wherein in said second hydrogenation zone, said hydrogenation is carried out at a temperature between 100° C. and 150° C.

8. The method according to claim 5, wherein in said first hydrogenation zone, said hydrogenation is carried out at a temperature between 50° C. and 80° C.

9. The method according to claim 8, wherein in said second hydrogenation zone, said hydrogenation is carried out at a temperature between 100° C. and 150° C.

10. The method according to claim 4, wherein the hydrogenation pressure in the two reaction zones is between 55 bar and 100 bar.

11. The method according to claim 5, wherein the hydrogenation pressure in the two reaction zones is between 50 bar and 150 bar.

12. The method according to claim 11, wherein the hydrogenation pressure in the two reaction zones is between 55 bar and 100 bar.

13. The method according to claim 6, wherein the hydrogenation pressure in the two reaction zones is between 50 bar and 150 bar.

14. The method according to claim 13, wherein the hydrogenation pressure in the two reaction zones is between 55 bar and 100 bar.

15. The method according to claim 7 wherein the hydrogenation pressure in the two reaction zones is between 50 bar and 150 bar.

16. The method according to claim 15, wherein the hydrogenation pressure in the two reaction zones is between 55 bar and 100 bar.

17. The method according to claim 9, wherein the hydrogenation pressure in the two reaction zones is between 50 bar and 150 bar.

18. The method according to claim 17, wherein the hydrogenation pressure in the two reaction zones is between 55 bar and 100 bar.

* * * * *